United States Patent [19]

Columbus

[11] Patent Number: 5,010,930
[45] Date of Patent: Apr. 30, 1991

[54] PIPETTE AND LIQUID TRANSFER APPARATUS FOR DISPENSING LIQUID FOR ANALYSIS

[75] Inventor: Richard L. Columbus, Rochester, N.Y.

[73] Assignee: Eastman Kodak Company, Rochester, N.Y.

[21] Appl. No.: 455,548

[22] Filed: Dec. 22, 1989

[51] Int. Cl.5 .......................... B65B 1/04; B67D 5/00
[52] U.S. Cl. .................................. 141/1; 141/238; 141/31; 141/242; 222/636
[58] Field of Search ................ 141/31, 234, 237, 238, 141/242, 243, 244, 245, 249, 67, 1; 222/636, 400.5; 604/246, 248, 140

[56] References Cited

U.S. PATENT DOCUMENTS

| | | | |
|---|---|---|---|
| 1,528,022 | 3/1925 | Keiser | 222/636 |
| 1,998,531 | 4/1935 | Werder | 141/234 |
| 3,227,312 | 1/1966 | Solvik et al. | 222/636 |
| 3,272,396 | 9/1966 | Neville, Jr. | 222/636 |
| 3,998,239 | 12/1976 | Kruishoop | 222/636 |
| 4,012,325 | 3/1977 | Columbus | 210/516 |
| 4,033,482 | 7/1977 | Kushner et al. | 222/636 |
| 4,340,390 | 7/1982 | Collins et al. | 23/230 B |
| 4,347,875 | 9/1982 | Columbus | 141/18 |
| 4,452,899 | 6/1984 | Alston | 436/46 |
| 4,615,360 | 10/1986 | Jacobs | 141/18 |
| 4,838,855 | 6/1989 | Lynn | 604/248 |

FOREIGN PATENT DOCUMENTS 438874  1/1975  U.S.S.R. .................. 222/636

Primary Examiner—Henry J. Recla
Assistant Examiner—Keith Kupferschmid
Attorney, Agent, or Firm—Dana M. Schmidt

[57] ABSTRACT

A combination of a pipette and a liquid transfer apparatus is disclosed. The liquid transfer apparatus comprises a frame defining a liquid inlet aperture connected by a first passageway to a dispensing aperture, an air vent aperture connected by a second passageway that extends toward the first passageway, and a valve interposed between the two passageways to alternate between allowing continuous liquid flow along the first passageway, or continuous air flow along the second passageway and part of the first passageway.

6 Claims, 3 Drawing Sheets

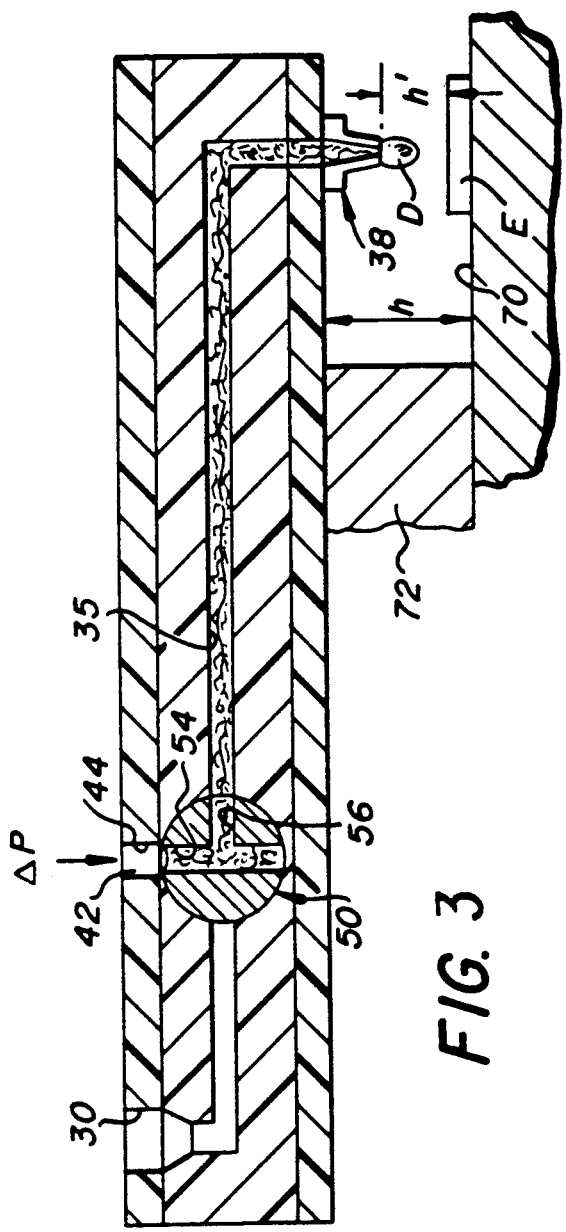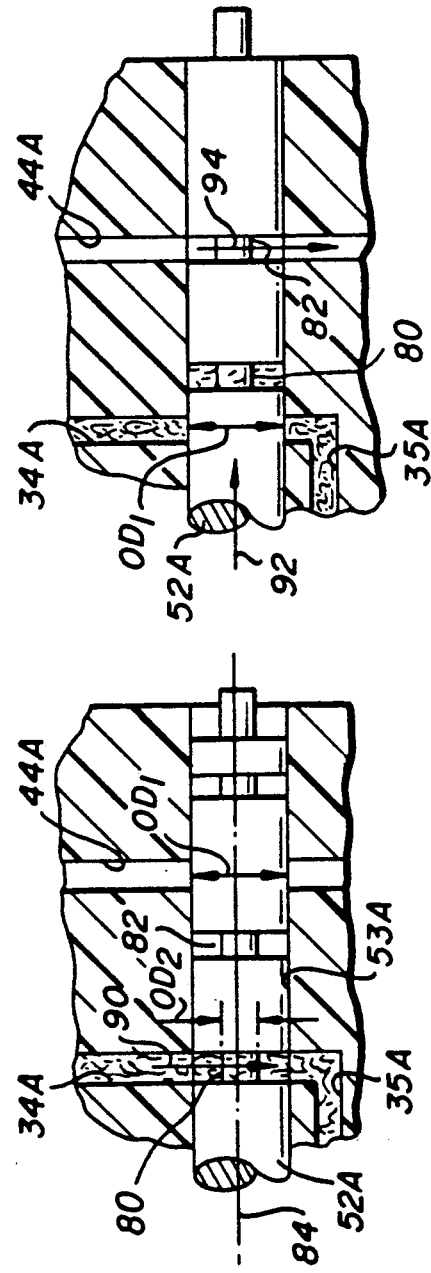

3,010,930

PIPETTE AND LIQUID TRANSFER APPARATUS FOR DISPENSING LIQUID FOR ANALYSIS

FIELD OF THE INVENTION

This invention relates to apparatus that allows any pipette to be used without careful control of manual positions, to accurately dispense small amounts of liquids for clinical analysis.

BACKGROUND OF THE INVENTION

The dispensing of aliquots of a body liquid such as blood serum onto a dried, slide like test element is a key first step in the analysis of the liquid in an analyzer. Because of the peculiar properties of many body liquids, and the need for accurate and reproducible dispensing of a predetermined aliquot, great care has been taken in prior art devices to ensure that (a) the proper tip is used by the dispensing apparatus to direct the flow properly, and/or (b) the dispensing tip is properly presented and positioned at the test element at the time of dispensing. Examples of the technology that achieve feature (a) include tips of the type described in U.S. Pat. No. 4,347,875. Examples of the technology used to achieve features (b) include dispensing means in analyzers of the type described in U.S. Pat. Nos. 4,340,390; 4,452,899 and 4,615,360. In the latter three, the analyzer is constructed, for example, to carefully prepare the dispensing tip Just prior to the dispensing, for example, in its spacing from the test element and/or by blowing off any exterior liquid hanging on the outside of the tip.

Such care as expressed by such technologies has worked well. However, they all require expensive, peculiar apparatus that is costly either in its construction or its use. Although this is not particularly disadvantageous when constructing an expensive, high-volume analyzer, it is a drawback when constructing an inexpensive, low-volume analyzer, such as might be needed or used in remote field locations.

Therefore, prior to this invention, there has been the need to provide an inexpensive interface that will allow a conventional pipette to dispense liquid that still flows onto the test element in a predictable, accurate manner.

SUMMARY OF THE INVENTION

I have constructed an interface and a method of using it that solve the aforementioned problems.

More specifically, in accord with one aspect of the invention, there is provided a liquid transfer apparatus in combination with any pipette for manually receiving liquid from the pipette at an inlet aperture and for automatically dispensing that liquid at a dispensing aperture onto a test element. The transfer apparatus comprises:

means defining an inlet aperture for liquid to be deposited into the apparatus, means defining a dispensing aperture for dispensing some of the liquid, means defining a first liquid flow path extending from the inlet aperture towards the dispensing aperture, means defining an air vent at the exterior of the apparatus and a second flow path extending from the vent towards the first flow path, and valve means interposed between the first and second flow paths for allowing continuous flow alternately from the inlet aperture to the aperture, or from the air vent to the dispensing aperture with the inlet aperture blocked.

In accord with another aspect of the invention, there is provided a method of dispensing accurately a predetermined amount of liquid onto a test element, comprising the steps of (a) injecting more than the predetermined amount from any pipette into a liquid transfer apparatus of the type set forth in the previous paragraph, the valve means being adJusted to allow continuous flow of liquid from the inlet aperture to the dispensing aperture, (b) moving the valve means to block flow between the inlet aperture and the dispensing aperture and to fluidly connect the liquid adjacent the dispensing aperture with the air vent, and (c) applying an amount of air pressure to the air vent that is effective to accurately dispense the predetermined amount of liquid out of the dispensing aperture.

Accordingly, it is an advantageous feature of the invention that any pipette can be used manually, and without careful control, to dispense accurate aliquots of a body liquid in the proper way onto a test element for assaying.

It is a related advantageous feature that an inexpensive interface is provided that receives any pipette positioned without great care, and dispenses liquid received from the pipette in the proper way.

Other advantageous features will become apparent upon reference to the following detailed description when read in light of the attached drawings.

BRIEF DESCRIPTION OF THE DRAWINGS

FIG. 3 is a section view similar to that of FIG. 2, illustrating the parts, however, as they are positioned for the dispensing step;

FIGS. 5A and 5B are fragmentary section views of the apparatus of FIG. 4, showing the valve in the alternative liquid filling position and the liquid dispensing position, respectively.

DESCRIPTION OF THE PREFERRED EMBODIMENTS

The invention is hereinafter described with respect to the Preferred embodiments, which feature the use of particular kinds of valves to control the two flow paths to dispense preferably blood serum or a reference liquid. Additionally, the invention is useful regardless of the type of liquid being dispensed and with apparatus using other kinds of valves, so long as the valve is effective to allow either the one flow path or the other flow path to be effective.

Figure 1:
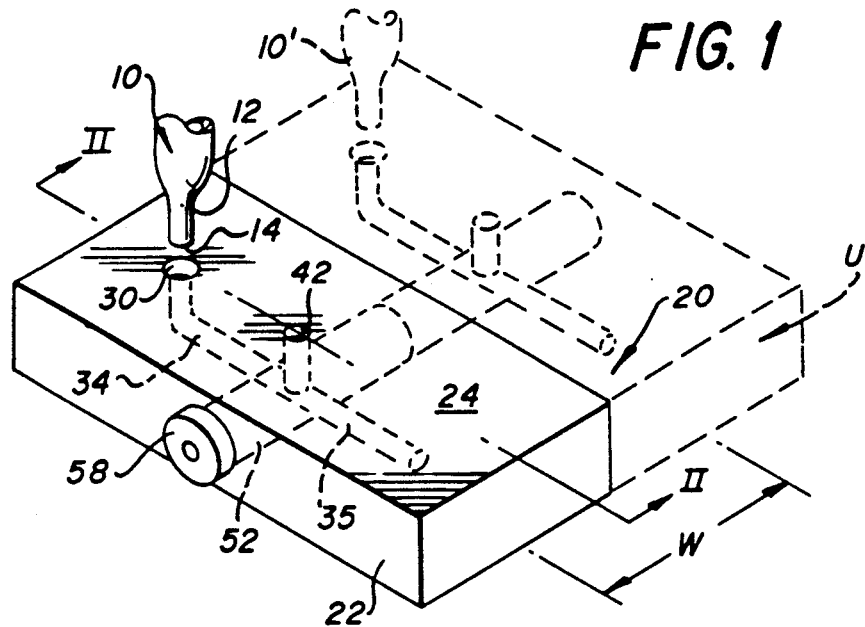
FIG. 1 is a fragmentary perspective view of the combination of the invention comprising a pipette and the liquid transfer apparatus.

As shown in FIG. 1, the combination of the invention features a pipette 10 and a liquid transfer apparatus 20. The pipette can be any pipette whatsoever, of any construction, conventional or otherwise, having a tip portion 12 with an outlet 14. Tip portion 12 can be fixed to or removable from the rest of the pipette.

Figure 2:
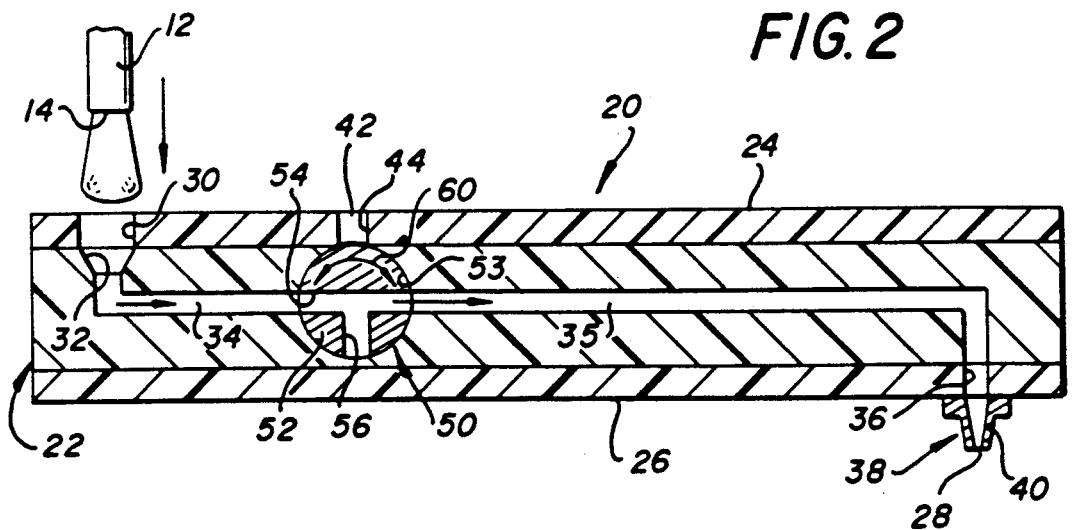
FIG. 2 is a vertical section view taken generally along the line II—II of FIG. 1.

It is because of the interface provided by apparatus 20 that it does not matter what pipette is used. Apparatus 20 comprises a frame 22, which can be any shape, a rectangular slab being shown by way of example. Top surface 24 is constructed to engage the pipette and a source of ΔP air pressure (not shown). A bottom surface 26, FIG. 2 is provided to supply a dispensing aperture 28 and a proper spacing from a test element E, FIG. 4, as described more hereinafter.

More specifically, top surface 24 has an inlet aperture 30, FIG. 1, shaped to receive tip portion 12 directly, or to receive liquid ejected therefrom. Preferably, the pipette is actually inserted, to seat on a surface 32 at the bottom of aperture 30, FIG. 2.

Aperture 30 fluidly connects with a fixed passageway 34, 35 that extends to an orifice 36 in surface 26. Valve 50 described hereinafter is disposed partway along passageway 34, 35. An appropriate dispensing tip 38 is mounted at orifice 36 to fluidly connect its aperture 28 with orifice 36.

Figure 4:
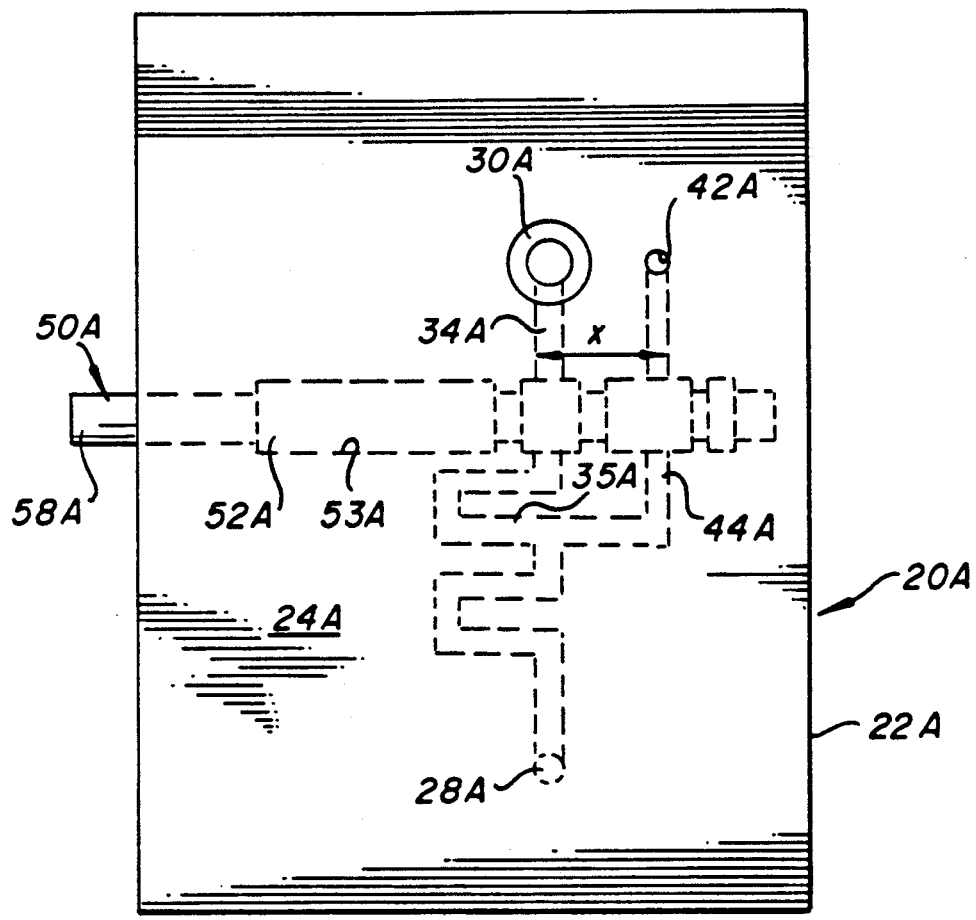
FIG. 4 is a plan view of another embodiment of the liquid transfer apparatus.

Any kind of tip 38 can be used, provided it is shaped to discourage perfusion up outside surface 40 thereof, and instead directs flow, such as a drop D, FIG. 4, onto the element. A useful example (not shown) is a tip configured as described in the aforesaid U.S. Pat. No. 4,347,875.

A vent aperture 42 is provided, such as in top surface 24, FIG. 2, and fluidly connects with a passageway 44 that extends towards passageway 34. Preferably, passageway 44 has a width sufficiently large as to discourage capillary attraction of liquid out of passageway 56.

Between the two passageways, valve 50 is interposed to allow, as alternatives, the completion of passageway 34–35 or the completion of passageway 44–35. A three way stop cock valve, here shown as cylindrically shaped, is useful. The valve comprises a cylinder 52, disposed in a bore 53, having a diameter passageway 54, a radial passageway 56 dead-ending on and 90° between passageway 54's outlets, and a handle means 58 exterior of frame 22 for rotating the valve, FIG. 1. Appropriate seals, not shown, are included to prevent axial leakage along the cylinder.

In use, valve 50 is rotated so as to appear as in FIG. 2, to connect passageway 34, 35 via passageway 54. As liquid is ejected from an inserted pipette, the liquid fills passageway 34, 35 until it reaches dispensing aperture 28.

Thereafter, cylinder 52 is rotated, arrow 60 or 60', until passageway 54 is aligned with passageway 44, AND passageway 56 is aligned with passageway 35, FIG. 3. Now valve 50 has blocked off the inlet aperture 30. The application of a pressure $\Delta P$ at aperture 42 will cause the dispensing of an aliquot of the liquid from passageway 35 and tip 38, onto element E. Most preferably, $\Delta P$ is generated from external air pressure delivered via means such as a hose, not shown, to aperture 42. (The hose is shaped to seal at aperture 42).

To insure that the proper dispensing height h' is achieved, surface 26 is positioned the proper height h above the support surface 70 of element E. Any suitable mechanism can be used to obtain such heights. For example, a spacer block 72 can be utilized, which can be a separate element or can be an integral part of apparatus 20.

Alternatively, apparatus 20 can be constructed to provide multiple transfer opportunities for a multiple number of pipettes containing each a different liquid, as is suggested in phantom, FIG. 1. That is, a plural number of passageways 34,35 can be provided in parallel, each with an inlet aperture 30, to accommodate a ganged pipette 10,10'. In such a construction, cylinder 52 can extend the full width of the entire device, so that handle means 58 is effective to rotate all the valves simultaneously. Such a construction is useful to allow the dispensing of, e.g., serum from pipette 10 and a reference liquid from pipette 10'. Particularly for such an example, the dispensing tips, of which only the first one 38 is depicted (FIG. 2), preferably would be spaced apart a distance w, FIG. 1, that would allow the simultaneous dispensing of serum and reference liquid onto a single ISE test element of the type shown in, e.g., U.S. Pat. No. 4,184,936.

Alternatively, (not shown), each of the separate passageways 34,35 can be valved separately from the others, in which case cylinder 52 would not extend across the entire unit. Instead, each passageway 34,35 would have its own cylinder and own operating handle means 58.

Still further, an additional option is to provide a temporary seal (not shown) over aperture 30 after liquid is inserted via the pipette, to allow storage in apparatus 20 before the dispensing step.

By reason of this transfer apparatus, the user need not be concerned about whether the pipette 10 has a tip 12 that is particularly suited for accurate dispensing (that is, will discourage perfusion). Nor need the user carefully position the pipette relative to any particular vertical position, since apparatus 20 automatically provides the correct height h' between the dispensing orifice and element E, FIG. 3. In fact, tips 38 can be different in length, if plural units U are ganged together, FIG. 1, and if a different height h' is needed at the adjacent apertures. For example, liquid used for radial wash preferably is applied with a height that is less than h' for serum dispensing.

It is not essential that the valve be a rotating type as shown. Alternatively, for example, it can be a spool valve, FIGS. 4–5B. Parts similar to those previously described bear the same reference numeral, to which the distinguishing suffix A is appended.

Thus, FIG. 4, apparatus 20A comprises a frame 22A providing a top surface 24A in which an inlet aperture 30A and a vent aperture 42A are provided, as in the previous embodiment. A passageway 34A,35A fluidly connects apertures 30A and 42A with a dispensing aperture 28A, via a valve 50A, also as in the previous embodiment. However, in this embodiment, valve 50A is a spool valve comprising a cylinder 52A that slides, rather than rotates, within bore 53A. Outer diameter $OD_1$, FIG. 5A, seals within bore 53A, whereas a reduced inner diameter $OD_2$ is provided at two locations 80, 82 spaced apart along axis 84 of cylinder 52A. The spacing of locations 80 and 82 is constructed to be less than the spacing "x", FIG. 4, of passageway 34A from passageway 44A that extends from the vent aperture 42A. In this embodiment, passageway 44A does not feed into the extension of passageway 34A,35A that occurs within the valve, but rather joins passageway 35A downstream from valve 50A. That is, there is no intersection of the air path and liquid path within the valve, as in the previous embodiment, but rather downstream thereof.

In use, cylinder 52A is slid so that reduced diameter $OD_2$ at location 80 is aligned with passageway 34A,35A, FIG. 5A, and liquid is inserted from the pipette (not shown), to provide continuous flow towards the dispensing aperture, arrow 90. In this position, cylinder 52A has $OD_2$ at location 82 misaligned with air passageway 44A. Thereafter, valve 50A is moved, using handle 58A, FIG. 4, by sliding cylinder 50A sideways, arrow 92, FIG. 5B, so that outer diameter $OD_1$ blocks any flow from passageway 34A to 35A, and at the same time $OD_1$ at location 82 becomes aligned with the parts of passageway 44A. This allows air pressure to flow continuously, arrow 94, from the air vent to passageway 35A, FIG. 4, and hence, to the liquid therein. That is, when valve 50A is positioned as shown in FIG. 5B, air pressure is applied continuously in an amount effective to accurately dispense a predetermined aliquot, for example 10 μl, of liquid out of the dispensing aperture.

Passageway 35A can be serpentine in its construction, as shown in FIG. 4, or it can be more linear in the manner of its construction shown in FIG. 2.

The invention has been described in detail with particular reference to certain preferred embodiments thereof, but it will be understood that variations and modifications can be effected within the spirit and scope of the invention.

What is claimed is:

1. Apparatus for dispensing liquid, comprising a pipette, and a liquid transfer apparatus for manually receiving liquid from said pipette at an inlet aperture and for automatically dispensing that liquid at a dispensing aperture onto a test element, said transfer apparatus comprising means defining said inlet aperture for liquid to be deposited into the apparatus, means defining said dispensing aperture for dispensing some of the liquid in droplet form, means defining a first liquid flow path extending from said inlet aperture towards said dispensing aperture, means defining an air vent at the exterior of the apparatus and a second flow path extending from said vent towards said first flow path, and valve means interposed between said first and second flow paths for allowing continuous flow alternately from said inlet aperture to said dispensing aperture, or from said air vent to said dispensing aperture with said inlet aperture blocked, said apparatus further including a first support adapted to support a test element with an upper surface that is to receive the liquid, a second support adapted to support said transfer apparatus, and means for accurately positioning said second support from said first support at a predetermined distance such that an initial droplet from said dispensing aperture contacts said upper surface while still in contact with said dispensing aperture to achieve proper dispensing of the liquid onto the test element.

2. Apparatus as defined in claim 1, wherein said valve is a rotating valve.

3. Apparatus as defined in claim 1 or 2, wherein said valve is interposed at the junction of said first and second flow paths.

4. Apparatus as defined in claim 1, wherein said valve is a sliding spool valve.

5. Apparatus as defined in claim 1 or 4, wherein said valve intersects said first and second paths at two different locations.

6. A method of dispensing accurately a predetermined amount of liquid onto a test element, comprising the steps of (a) injecting more than said predetermined amount from a pipette into a liquid transfer apparatus comprising means defining an inlet aperture for liquid to be deposited into the apparatus, means defining a dispensing aperture for dispensing some of the liquid, means defining a first liquid flow path extending from said inlet aperture towards said dispensing aperture, means defining an air vent at the exterior of the apparatus and a second flow path extending from said vent towards said first flow path, and valve means interposed between said first and second flow paths for allowing continuous flow alternately from said inlet aperture to said dispensing aperture, or from said air vent to said dispensing aperture with said inlet aperture blocked, said valve means being adjusted to allow continuous flow of liquid from said inlet aperture to said dispensing aperture, (b) moving said valve means to block flow between said inlet aperture and said dispensing aperture and to fluidly connect the liquid adjacent the dispensing aperture with said air vent, and (c) applying an amount of air pressure to said air vent that is effective to accurately dispense said predetermined amount of liquid out of said dispensing aperture.

* * * * *